(12) United States Patent
Tamiya et al.

(10) Patent No.: US 8,110,406 B2
(45) Date of Patent: Feb. 7, 2012

(54) ANALYTICAL METHOD AND ANALYTICAL APPARATUS

(75) Inventors: Eiichi Tamiya, Kanazawa (JP); Naoki Nagatani, Hakusan (JP); Teruko Yui, Kanazawa (JP); Tatsurou Endou, Nomi (JP); Ryou Tanaka, Nomi (JP)

(73) Assignees: Japan Advanced Institute of Science and Technology, Ishikawa (JP); Bio Device Technologies Co., Ltd., Ishikawa (JP)

( * ) Notice: Subject to any disclaimer, the term of this patent is extended or adjusted under 35 U.S.C. 154(b) by 337 days.

(21) Appl. No.: 12/085,466

(22) PCT Filed: Nov. 27, 2006

(86) PCT No.: PCT/JP2006/323617
§ 371 (c)(1),
(2), (4) Date: Jul. 18, 2008

(87) PCT Pub. No.: WO2007/061098
PCT Pub. Date: May 31, 2007

(65) Prior Publication Data
US 2009/0047746 A1 Feb. 19, 2009

(30) Foreign Application Priority Data
Nov. 25, 2005 (JP) ................................. 2005-341256

(51) Int. Cl.
*G01N 33/53* (2006.01)
(52) U.S. Cl. ......... 436/518; 435/7.1; 435/7.5; 435/7.93; 435/7.95; 435/287.1; 435/287.7; 435/287.9; 435/970; 436/514

(58) Field of Classification Search .................... 435/7.1, 435/7.5, 7.93, 7.94, 7.95, 287.1, 287.7, 287.8, 435/287.9, 970; 436/514, 518; 977/700, 977/773, 788, 918
See application file for complete search history.

(56) References Cited

U.S. PATENT DOCUMENTS

| 5,141,850 | A | * | 8/1992 | Cole et al. ..................... 436/525 |
| 5,618,732 | A | | 4/1997 | Pease et al. |
| 6,103,538 | A | * | 8/2000 | Kotsugai ....................... 436/536 |
| 2002/0151041 | A1 | * | 10/2002 | Kreimer et al. ............. 435/287.2 |
| 2003/0134333 | A1 | | 7/2003 | Dehlinger et al. |

FOREIGN PATENT DOCUMENTS
JP S55-116258 6/1980
(Continued)

*Primary Examiner* — Bao Thuy L Nguyen
(74) *Attorney, Agent, or Firm* — Manabu Kanesaka (57) ABSTRACT

[PROBLEMS] To reduce the amount of, for example, a capturing antibody to be employed without lowering detection sensitivity. At the same time, to enable the achievement of intense color development or light emission in a determination area even in the case where only a small amount of a labeled antibody is accumulated. To lower the detection limit in the sandwich method. To enlarge the dynamic range in the competition method. [MEANS FOR SOLVING PROBLEMS] A method of analyzing a test substance by an immunological analysis method by using the test substance, a support having a determination area, on which one member selected from a capturing antibody capable of binding specifically to the test substance and a capturing antigen capable of binding specifically to the test substance has been immobilized, and a labeled antibody capable of binding specifically to the test substance, wherein a label having a sensitizing effect has been immobilized on the determination area of the support.

10 Claims, 5 Drawing Sheets

A

FOREIGN PATENT DOCUMENTS

| | | |
|---|---|---|
| JP | H05-196616 | 8/1993 |
| JP | H06-043162 | 2/1994 |
| JP | 2002-202307 | 7/2002 |
| JP | 2002-214237 | 7/2002 |
| JP | 2002-372531 | 12/2002 |
| WO | WO 88/08534 | * 11/1988 |

* cited by examiner

ANALYTICAL METHOD AND ANALYTICAL APPARATUS

TECHNICAL FIELD

This invention relates to a method and an apparatus for analyzing a specimen in accordance with the immunoassay method.

BACKGROUND ART

As a means for detecting a trace of a specimen in a sample, the immunoassay method has been heretofore known. Among other methods, the ELISA (enzyme-linked immunosorbent assay) method has been widely disseminated owing to its capability of implementing the detection with high sensitivity. The ELISA method nevertheless entails such problems as necessitating protraction of the time for an operation and the time for a reaction and as well complicating the operation of determination.

In recent years, therefore, as immunoassay methods that promise to take the place of the ELISA method, the immunochromatography method that comprises causing a test solution to be absorbed in one end of a membrane having an antibody fixed thereon and enabling the test solution to be gradually spread in the lateral direction by means of capillarity and the flow-through method that causes a membrane having an antibody fixed thereon to pass a test solution therein in the direction of thickness of the membrane have been attracting attention. In particular, the immunochromatography method excels in various points such as smallness and eminent portability of an apparatus (strip) and superiority over the ELISA method in stability of preservation, rapidity of determination, easiness of judgment, and obviation of the necessity for a special attachment. Thus, the immunochromatography method is popularly used in the field of diagnostic drugs for testing patients for influenza, for HCV, for pregnancy, for allergy, and for food poisoning, for example.

The immunochromatography method that utilizes a sandwich process is carried out as follows, for example. First, two kinds of antibodies capable of recognizing different regions of a specimen and a strip of membrane are prepared; one kind of antibody (capturing antibody) is immobilized in advance in a region of the membrane called a test line and the other kind of antibody is transformed, via labeling with colloidal particles, for example, into a gold colloid-conjugated antibody. Then, a test solution is mixed with the gold colloid-conjugated antibody and the strip is caused to absorb the resultant mixture in one end thereof and spread it therein. When the test solution happens to contain a specimen, the specimen reacts with the gold colloid-conjugated antibody to form a specimen-gold colloid-conjugated antibody complex and this complex, while passing on the test line, is captured by the capturing antibody to form a capturing antibody-specimen-gold colloid-conjugated antibody complex. As a result, the gold colloid-conjugated antibody is observed to develop a red color on the test line.

The immunochromatography method mentioned above embraces a widely known process that comprises labelling an antibody with such an enzyme as an alkali phosphatase or a peroxidase in the place of the colloidal gold particles and having a color developing agent subsequently spread in the marked antibody. Patent Document 1, for example, proposes a method for carrying out enzymatic immunoassay in the presence of a base in the determination of enzymatic immunity using a peroxidase. Then, Patent Document 2 proposes an apparatus for chromatographic assay where an antibody-immobilized part having immobilized thereon an antibody capable of specifically combining with a specimen under assay and a pigment-immobilized part having an optional pigment immobilized thereon coexist at one position Patent Document 1: JP-A 2001-0074740
Patent Document 2; JP-A 2001-004613

DISCLOSURE OF THE INVENTION

Problem to be Solved by the Invention

The immunochromatography method that uses the gold colloid-conjugated antibody, however, is such that the detection of a specimen having an extremely low concentration may become difficult at times. This is because the intensity of the signal (color development) originating in the gold colloid-conjugated antibody in the region where a capturing antibody has been immobilized does not reach such a level as is discernible with an unaided eye when the concentration of a specimen in a test solution is extremely low and hence the amount of the gold colloid-conjugated antibody accumulated on the test line becomes small.

Thus, studies aimed at heightening the sensitivity of detection of the immunochromatography method are being promoted in various fields. The technique for causing an antibody under assay to develop a color by labelling the antibody with an enzyme and spreading the relevant enzyme-substrate as disclosed in Patent Document 1 cited above has been adopted for practical use as a measure for the improvement implied above. This technique, however, has the disadvantage of complicating analysis on account of the necessity of subsequently spreading a color-developing agent for the purpose of detection.

Since this technique also necessitates preparatory immobilization of the capturing antibody on the test line, the expensiveness of the antibody constitutes one of the causes for boosting the cost of the material for the immunochromatography strip. In spite of the consequent urgent need for a decrease in the amount of the capturing antibody to be used for the immunochromatography strip, the mere decrease of the amount of the capturing antibody entails the disadvantage of degrading the sensitivity of detection.

Meantime, the immunoassay method that uses a competitive process poses as a problem the difficulty encountered in securing a dynamic range in a region of high concentration because the amount of a gold colloid-conjugated antibody to be accumulated in a region having immobilized a capturing antibody decreases in accordance as the concentration of a specimen increases.

Incidentally, Patent Document 2 discloses an apparatus for chromatography assay having a pigment and an antibody immobilized in a mixed state. The pigment involved herein is used for the purpose of enabling the position of the antibody immobilized part to be perceived as by visual observation and consequently preventing misregistration of the part being judged during the work of assembly. The acquisition of the effect of sensitization of the assay is not contemplated by the relevant invention.

This invention has been proposed in view of the actual state of affairs mentioned above and is aimed at providing an analytical method and an analytical apparatus that anticipate decreasing the amount of a capturing antibody to be used without inducing degradation of the sensitivity of detection, enable acquisition of strong color development or light emission on a test line even when the amount of a labeled antibody to be accumulated is small, and allow the sandwich process to lower the detection limit and the competitive process to enlarge the dynamic range.

Means to Solve the Problem

The analytical method contemplated by this invention for the solution of the problem mentioned above is a method for analyzing a specimen by an immunoassay process that uses a supporting body possessing a test line having immobilized one member selected from the group consisting of a specimen, a capturing antibody specifically combining with the specimen, and a capturing antigen specifically combining with the specimen and a marker antibody specifically combining with the specimen and this method is characterized by the fact that the test line of the supporting body has immobilized in advance a marker substance possessing a sensitizing action.

The analytical apparatus contemplated by this invention is an apparatus for analyzing a specimen by an immunoassay process that contains a supporting body possessing a test line having immobilized one member selected from the group consisting of a specimen, a capturing antibody specifically combining with the specimen, and a capturing antigen specifically combining with the specimen and this apparatus is characterized by the fact that the test line of the supporting body mentioned above has immobilized in advance a marker substance possessing a sensitizing action.

In the case of the conventional immunoassay method that uses a sandwich process having a capturing antibody immobilized on a supporting body, for example, the region (test line) having the capturing antibody immobilized is enabled to accumulate a labeled antibody thereon by having the capturing antibody, a specimen, and the labeled antibody form a complex shaped like a sandwich. When the labeled antibody has accumulated on the test line beyond a prescribed volume, it is made possible to discern color development or light emission by visual observation or detect it with an instrument and know the presence of the specimen. If the specimen has an extremely low concentration and the accumulation of the labeled antibody consequently becomes insufficient, however, the color development or the light emission will possibly be too feeble to be discerned by visual observation or detected by mechanical analysis.

In this invention, since the marker substance possessing a sensitizing action is immobilized in advance on the test line, the color development or the light emission on the test line amounts to the sum of the marker substance originating in the labeled antibody accumulated on the test line and the marker substance immobilized in advance and possessing a sensitizing action. That is, the intensity of the color development or the intensity of the light emission in the test line is exalted. As a result, detection of a specimen at a concentration lower than has ever been the case before is realized because the amount of a labeled antibody (marker substance) necessary for enabling the intensity of color development or the intensity of light emission to be detected by visual observation or with an instrument is allowed to be small as compared with the conventionally ordinary amount. Where the conventional analytical method having only a capturing antibody immobilized on a supporting body is enabled to detect color development of a labeled antibody by allowing 100 or more pieces of the labeled antibody to accumulate, for example, this invention enables the detection of the color development to be accomplished by having 80 pieces of a marker substance immobilized in advance together with a capturing antibody on a supporting body and consequently allowing 20 or more pieces of a labeled antibody to accumulate. By the immunoassay method using a sandwich process, the same effect as the above statement is obtained when a capturing antigen is immobilized on a supporting body in the place of a capturing antibody. In this case, the complication of the analytical operation can be repressed because such materials as enzymes that require careful handling are not needed.

Further, in the case of the sandwich process, the amount of a capturing antibody or the amount of a capturing antigen that is required in realizing prescribed sensitivity is allowed to be smaller than has been heretofore the case because the sensitivity is exalted as described above. The effect of reducing the cost, therefore, is obtained when a capturing antibody, for example, is immobilized on the test line.

On the other hand, in the immunoassay method using a competitive process, the amount of a labeled antibody accumulated on the test line is decreased and the color development or the light emission is weakened in accordance as the concentration of a specimen is heightened. In this invention, by having a marker substance possessing a sensitizing action immobilized in advance on a supporting body together with a specimen, it is made feasible to raise the intensity of color development or the intensity of light emission and decrease the amount of a labeled antibody (marker substance) required for enabling the color development or the light emission to reach a detectable level. As a result, the competitive process is enabled to realize the detection of a specimen in a region of a higher concentration and realize quantitative analysis of a wide dynamic range.

Effect of the Invention

By this invention, it is made possible to obtain sufficiently high intensity of color development or light emission and facilitate the detection thereof by visual observation or with an instrument even when the accumulation of a labeled antibody on the test line is not sufficient. As a result, it is made feasible to realize exalted sensitization in the case of the immunoassay method using a sandwich process and realize quantitative analysis in a wide dynamic range in the case of the immunoassay method using a competitive process. It is further made feasible to decrease the amount of a capturing antibody to be immobilized on the supporting body without inducing degradation of the sensitivity of detection and realize lowering the cost of the analytical apparatus.

EXPLANATION OF REFERENCE NUMERALS

1. Specimen, 2. capturing antibody, 3. antibody, 4. supporting body, 5. marker substance, 6. labeled antibody, 7. marker substance, 11. immunochromatography strip, 12. supporting body, 13. conjugate pad, 14. absorption pad, 15. test line, 16. control part, 21. capturing antibody, 22. marker substance, 23. labeled antibody, 24. control antibody

BEST MODE OF EMBODYING THE INVENTION

Now, the analytical method and the analytical apparatus that embody this invention will be described in detail below with reference to the drawings.

The analytical method of this invention is directed to analyzing a specimen in a test solution by an immunoassay process using a supporting body possessing a test line having immobilized one member selected from the group consisting of a specimen, a capturing antibody specifically combining with a specimen, and a capturing antigen specifically combining with a specimen and a labeled antibody specifically combining with a specimen and is required to have immobilized in advance on the test line of the supporting body a marker substance possessing a sensitizing action.

Figure 1:
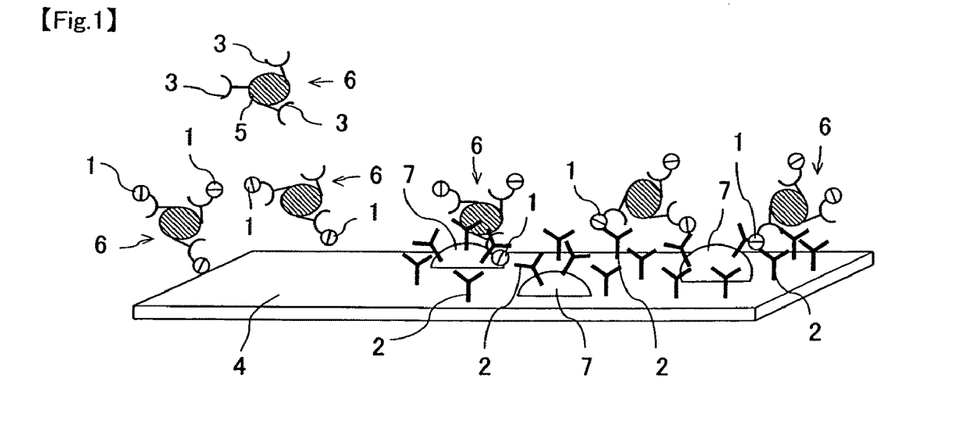
FIG. 1 This is a schematic perspective view of the essential part depicting one example of the analytical method of this invention.

The analytical method of this invention will be explained herein below by citing as an example the immunoassay method using a sandwich process that comprises immobilizing a capturing antibody on a supporting body and subjecting a specimen to qualitative analysis or quantitative analysis by causing a labeled antibody and the capturing antibody to be combined in the form of a sandwich with the specimen and as well referring to FIG. 1 and FIG. 2. Incidentally, FIG. 1~FIG. 3 are drawn in dimensional ratios different from those in actual existence.

The immunoassay method employing the sandwich process uses two kinds of antibody 2, 3 that severally recognize different regions on a specimen (antigen) 1. One of the two kinds of antibody (capturing antibody) 2 is immobilized on a supporting body 4. The region in which the capturing antibody 2 is immobilized constitutes a test line. The other kind of antibody 3 is not immobilized on the supporting body 4 but is labeled with a marker substance 5 to form a labeled antibody 6. In this invention, a marker substance 7 possessing a sensitizing action is immobilized in advance on the test line mentioned above.

In order to detect the specimen 1 in the test solution, first the test solution and the labeled antibody 6, for example, are mixed to form a composite of the specimen 1 and the labeled antibody 6 and this composite is subsequently supplied to the supporting body 4. In case the immunochromatography method is to be utilized, the supporting body 4 is made to absorb the test solution (mixed liquid) at one end thereof and enable the test solution to be spread in the lateral direction by means of capillarity In case the flow-through method is to be utilized, the test solution is added dropwise to the surface of the supporting body 4 and then caused to pass through the supporting body 4 to the surface on the opposite side. Otherwise, the test solution and a solution containing the labeled antibody 6 may be severally supplied to the supporting body 4 in the order mentioned. In case the specimen 1 is present in the test solution, the capturing antibody 2 and the labeled antibody 6 immobilized on the supporting body 4 are combined in the form of a sandwich with the specimen 1 and, as a result, the labeled antibody 6 is accumulated on the test line 6 in an amount corresponding to the specimen 1.

Figure 2:
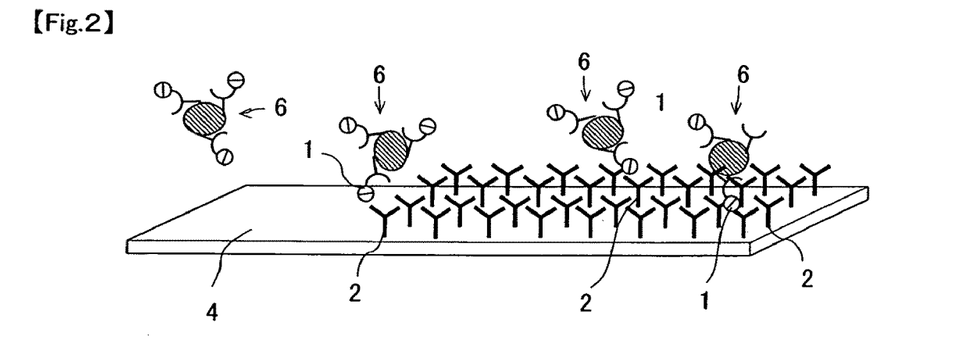
FIG. 2 This is a schematic perspective view of the essential part depicting one example of the conventional analytical method.
Figure 3:
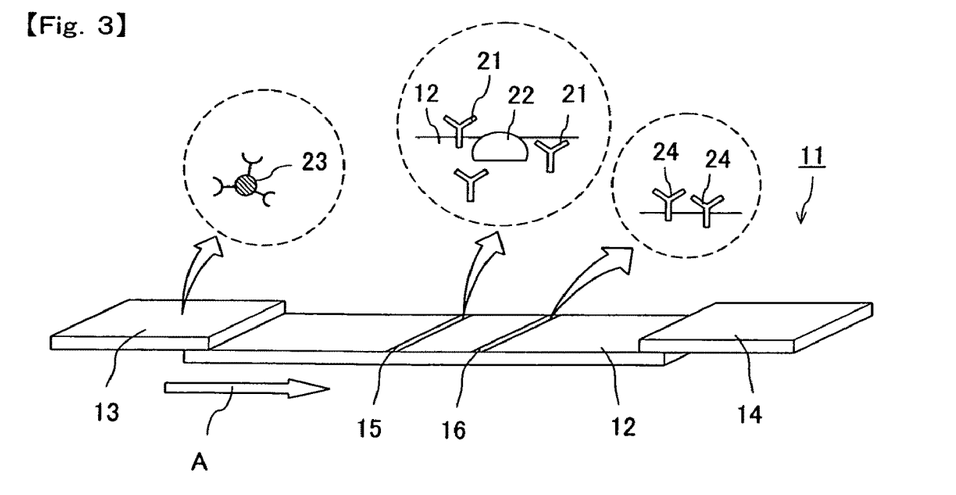
FIG. 3 This is a schematic perspective view depicting an immunochromatography strip as one example of the analytical apparatus of this invention.

In the case of the conventional method, the labeled antibody 6 accumulated on the test line is also in a small amount when the specimen has an extremely low concentration as illustrated in FIG. 2. Thus, the specimen 1 cannot be detected sometimes when the intensity of the signal (color development or light emission) originating in the marker substance 5 constituting the labeled antibody 6 does not reach a level necessary for recognition by visual observation or falls short of the detection limit of mechanical analysis.

In contrast, this invention is capable of raising the intensity of color development or the intensity of light emission on the test line by inducing the coexistence of the capturing antibody 2 and the marker substance 7 possessing a sensitizing action on the test line. The presence of the immobilized marker substance 7 results in making denser the gaps between the adjacent particles of the marker substance. Even when the labeled antibody 6 is accumulated in a small amount on the test line, therefore, it is made possible to exalt the intensity of color development or the intensity of light emission on the test line and realize the analysis with high sensitivity.

The expression "marker substance possessing a sensitizing action" as used herein refers to a marker substance that exhibits an effect of shifting the color development or light emission on the test line in the enhancing direction when the labeled antibody is captured and accumulated on the test line having the marker substance immobilized thereon.

As the marker substance 7 possessing a sensitizing action, a color-developing substance or light-emitting substance can be used as a marker substance and the color-developing substance is preferably used because it is capable of rapid and simple detection.

As concrete examples of the color-developing substance usable herein, finely divided metal particles, finely divided plastic particles, finely divided organic polymer particles, finely divided inorganic particles, and finely divided color-developing particles of liposome including a color-developing agent may be cited. As examples of the finely divided metal particles, finely divided noble metal particles such as finely divided gold particles, finely divided silver particles, and finely divided platinum particles, finely divided titanium particles, finely divided iron particles, and finely divided nickel particles may be cited. The finely divided metal particles may be finely divided metal particles in a colloidal state having a particle diameter of 1 nm~100 nm. That is, noble metal colloidal particles such as colloidal gold particles, colloidal silver particles, and colloidal platinum particles and colloidal titanium particles, colloidal iron particles, and colloidal nickel particles may be used. As finely divided latex particles, the finely divided particles containing at least one member selected from the group consisting of polystyrene, styrene-styrene sulfonate copolymer, methacrylic acid polymer, acrylic acid polymer, acrylonitrile-butadiene-styrene copolymer, vinyl chloride-acrylic ester copolymer, and vinyl acetate-acrylic ester copolymer may be cited. As the finely divided organic polymer particles, the finely divided particles containing at least one member selected from the group consisting of insoluble agarose, cellulose, and insoluble dextran may be cited. As finely divided inorganic particles, silica and alumina may be cited. Among other examples cited above, the colloidal noble metal particles and the finely divided latex particles that abound in general-purpose properties are preferably used and the finely divided gold particles that are capable of generating a clear color are used particularly preferably.

The surface of such a marker substance as this may be made to absorb polyethylene glycol, alkyl thiol, biotin, avidin, or nucleic acid to form a protective layer. When the marker substance consists of colloidal metal particles, for example, the possibility that the protective layer, when immobilized on the supporting body, will be mistaken as a background is diminished because the protective layer prevents the colloidal particles from aggregating.

If the marker substance 7 possessing a sensitizing action is immobilized in a high concentration on the test line of the supporting body 4, the detection with due accuracy may possibly become difficult because the color development or light emission originating in the marker substance 7 forms a background. When the detection or quantitative determination of the specimen is implemented by causing the color development or light emission of the test line to be recognized with an unaided eye, therefore, the amount of the marker substance 7 to be immobilized on the test line is preferred to be such that the recognition by visual observation may become impracticable. Inasmuch as the color development or light emission of the marker substance on the test line is incapable of being recognized by visual observation, the analysis with due accuracy is realized because the color development or light emission originating in the immobilized marker substance poses no obstruction during the course of detection.

When the detection or quantitative determination of the specimen is implemented by causing the color development or light emission on the test line to be detected by the use of an instrument such as a densitometer, the amount of the marker substance 7 to be immobilized on the test line is preferred to fall short of the detection limit of the instrument. So long as the color development or light emission of the marker substance on the test line falls short of the detection limit of the instrument being used in the analysis, the analysis with due accuracy is materialized because the color development or light emission originating in the immobilized marker substance 7 poses no obstruction during the course of detection.

When colloidal gold particles are used as the marker substance 7 possessing a sensitizing action, the colloidal gold particles are preferred to have a particle diameter of 10 nm~80 nm from the viewpoint of accomplishing the determination with high accuracy and high sensitivity. If the colloidal gold particles to be used have a particle diameter that deviates from the range mentioned above, the effect of enhancing the sensitivity will possibly prove to be insufficient. By using colloidal gold particles having a particle diameter of 15 nm~40 nm, it is made feasible to accomplish the detection with higher sensitivity.

As the marker substance 7 possessing a sensitizing action, a material that is congeneric with the marker substance 5 constituting the labeled antibody 6 can be used. When the congeneric material is used, the sensitizing effect can be obtained without fail because the marker substance 7 possessing a sensitizing action and the marker substance 5 constituting the labeled antibody 6 severally emit nearly identical signals. Further, the fact that the marker substance 7 possessing a sensitizing action and the marker substance 5 constituting the labeled antibody 6 are made to constitute congeneric materials is at an advantage in facilitating the procurement of materials. When congeneric materials are used for the immobilized marker substance 7 and the marker substance 5 constituting the labeled antibody 6, the sizes (particle diameters) thereof may be or may not be identical. When the finely divided color-developing particles are made to possess mutually different particle diameters, the variation (peak shift) of the wavelength of color development or the variation of the intensity of the wavelength of color development is observed. In the case of this nature, the present specification presumes use of congeneric materials.

The marker substance 7 possessing a sensitizing action and the marker substance 5 constituting the labeled antibody 6 may be xenogeneric materials. The combination in this case may be selected arbitrarily so long as it is capable of acquiring a due sensitizing effect. As examples of the combination, finely divided silver particles-finely divided gold particles, finely divided gold particles-latex particles, finely divided gold particles-fluorescent particles, xenogeneric fluorescent particles, colloidal gold particles-liposome including silver particles, and proteinaceous color-developing agent-liposome including silver particles may be cited.

Though the method for immobilizing the marker substance 7 possessing a sensitizing action on the supporting body 4 properly varies in conformity with the materials to be used, it is aptly carried out by modifying the capturing antibody 2 with the marker substance 7 thereby preparing a labeled capturing antibody that is the complex of the marker substance 7 and the capturing antibody 2 and subsequently coating the supporting body 4 with a solution containing the labeled capturing antibody. The amount of the marker substance 7 to be immobilized on the supporting body 4 in this case can be controlled by causing the solution to contain the capturing antibody 2 (non-labeled capturing antibody) incapable of being labeled by the marking substance together with the marked capturing antibody so that the ratio between the labeled capturing antibody and the non-labeled capturing antibody may be varied. By having the supporting body 4 coated in the state of the labeled capturing antibody, the marker substance 7 is stably immobilized because the capturing antibody 2 fulfils such a role as induces adhesion between the marker substance 7 and the supporting body 4. As a result, the detection of the specimen 1 can be infallibly effected as compared with the case of separately applying the marker substance 7 and the capturing antibody 2 because the test solution is prevented from forcing the marker substance 7 to drop off the supporting body 4 and flow downstream.

The method for immobilizing the marker substance 7 possessing a sensitizing action on the supporting body 4 may comprise mixing the marker substance 7 with the solution of a proteinaceous substance thereby causing the marker substance 7 to be combined with the proteinaceous substance and subsequently applying the resultant solution to the supporting body 4. As the proteinaceous substance to be combined with the marker substance 7, bovine serum albumin (BSA) may be cited for example. This method is useful in causing an antigen and a specimen having a small molecular weight to be immobilized together with the marker substance 7 on the test line of the supporting body 4.

As the marker substance 5 to be used for constituting the labeled antibody 6, any of the aforementioned substances that are usable as the marker substance 7 to be immobilized on the supporting body 4 can be used. The preparation of the labeled antibody 6 from the marker substance 5 and the antibody 3 may be effected by following the ordinary method that is satisfactorily accomplished by mixing the marker substance 5 constituting the labeled antibody 6 with the antibody 3 in a buffer solution, for example. Besides, the combination that uses biotin-avidin and thiol group can be utilized.

This invention allows adoption of all conceivable substances including organic substances and synthetic substances as the specimen 1. Also as the test solution containing the specimen 1, the solutions such as blood, serum, and urine originating in living organisms, the solutions containing water and soil collected from the natural environment, and the solutions prepared by using such solutions can be arbitrarily used, for example.

Now, the analytical apparatus to be used for the purpose of performing such an analysis as described above will be explained below. FIG. 3 portrays one example of the immunochromatography strip that embodies this invention. An immunochromatography strip 11 illustrated in FIG. 3 is provided with a supporting body 12 formed in the shape of a strip, a conjugate pad 13 disposed on the upstream side of the supporting body 12, and an absorption pad 14 disposed on the downstream side.

As the supporting body 12, the membranes that are usable at all in the immunochromatography process of this kind can be used unlimitedly. For example, nitrocellulose can be used. The supporting body 12 is provided at the halfway point thereof with a test line 15 that serves as a region for allowing immobilization of a capturing antibody 21. Though the test line 15 is formed in the shape of a belt nearly perpendicular to the direction of development, for example, as illustrated in FIG. 1, it does not need to be limited to this shape. It may be formed in an arbitrary shape such as, for example, the shape of a spot. On the test line 15 of the immunochromatography strip 11 of this invention, a marker substance 22 possessing a sensitizing action is immobilized together with the capturing antibody 21.

The conjugate pad 13 disposed on the upstream side of the test line 15 of the supporting body 4 holds a labeled antibody 23 in a movable (spreadable) state. The conjugate pad 13 is made to assume such a structure that filter paper excelling in water absorbing property, for example, is superposed on the upper surface of glass wool having the labeled antibody 23 retained therein. By having the labeled antibody 23 retained spreadably on the upstream side of the test line 15, it is made possible to complete the operation of analysis with one step of spreading the test solution. To be specific, the operation can be simplified by obviating the necessity for performing a step of separately spreading the labeled antibody 23 subsequent to spreading the test solution or a step of mixing the test solution and the labeled antibody 23 prior to spreading them.

Incidentally, the immunochromatography strip of this invention does not find the conjugate pad 13 that retains the labeled antibody 23 as an indispensable entity. If the supply lacks the conjugate pad 13, the act of supplying the supporting body 12 with the mixed solution between the test solution and the labeled antibody 23 or the act of supplying the supporting body 12 with the test solution and a solution containing the labeled antibody 23 sequentially in the order mentioned will suffice.

The supporting body 12 is provided on the downstream side of the test line 15 with a control part 16 adapted to capture the labeled antibody 23 that has escaped being captured by the test line 15. The control part 16 is formed by fixing on the supporting body 12 a control antibody 24 capable of recognizing the labeled antibody 23. The termination of the test is indicated by the color development or light emission that occurs in the labeled antibody 23 captured by the control part 16.

The absorption pad 14 is enabled, by being disposed on the downstream side of the test line 15 and the control part 16 of the supporting body 4, to absorb an excess of the test solution, for example.

The first step in executing the analysis by the use of the immunochromatography strip 11 of the foregoing description consists in causing the conjugate pad 13 to absorb the test solution. When the specimen is present in the test solution, the fact that the test solution passes through the conjugate pad 13 results in causing the labeled antibody 23, while moving toward the supporting body 12, to react with the specimen and form the composite between the specimen and the labeled antibody 23. The test solution continues to spread in the lateral direction as indicated by the arrow mark A by virtue of capillarity and gets captured by the capturing antibody 21 while the composite mentioned above is passing through the test line 15. That is to say, the composite of the capturing antibody 21, the specimen, and the labeled antibody 23 is formed and the marker substance constituting the labeled antibody 23 is accumulated on the test line 15. Since the marker substance 22 possessing a sensitizing action has been immobilized in advance on the test line 15, the color development or light emission on the test line 15 amounts to the sum between the marker substance forming the labeled antibody 23 accumulated on the test line and the marker substance 22 immobilized in advance. As a result, even when the labeled antibody 23 accumulated on the test line 15 is in a small amount, it is made possible to increase the color development or light emission on the test line and realize the exaltation of sensitivity. Further, by having the marker substance 22 possessing a sensitizing action immobilized in advance on the test line 15, it is made possible to decrease the amount of the capturing antibody 21 required to be immobilized for the purpose of obtaining the same sensitivity as in the case of omitting the immobilization of the marker substance 22. Thus, the advantage that the cost of the immunochromatography strip 11 is lowered is also obtained.

Since the immunochromatography strip 11 of this invention is capable of effecting analysis with such high sensitivity as has been heretofore attained only by the ELISA process, it can be made applicable to the field in which the ELISA process is finding general-purpose applications. Besides, since the time required by the analysis with the immunochromatography strip 11 of this invention is on the order of several minutes, for example, this analysis is advantageous in terms of reducing the time of analysis over the analysis by the ELISA process that requires several hours.

By this invention, not only the qualitative analysis of a specimen but also the quantitative analysis of a specimen in a test solution can be executed. The quantitative analysis can be carried out, for example, by finding in advance the correspondence between the concentration of a specimen and the intensity of color development or light emission and comparing the values of intensity of color development or intensity of light emission of the test line before and after the analysis.

Incidentally, when a capturing antigen capable of being specifically combined with a specimen (antibody) is immobilized in place of the capturing antibody on the supporting body and the antibody is detected as the specimen by the sandwich process, the same effect is obtained as in the case of having the aforementioned capturing antibody immobilized. The immobilization of the capturing antigen on the supporting body is preferably accomplished by mixing the marker substance possessing a sensitizing action with the solution of a proteinaceous substance thereby combining the marker substance with the proteinaceous substance and subsequently coating the supporting body with the resultant solution. By this procedure, the marker substance possessing a sensitizing action can be stably immobilized on the supporting body. As the proteinaceous substance to be combined with the marker substance, bovine serum albumin may be cited, for example.

While the example of adopting the immunochromatography process as an immunoassay method has been explained above, this invention also allows adoption of the so-called flow-through process The term "flow-through process" refers to a procedure that comprises causing a test solution to pass through a supporting body in the direction of thickness of a membrane and subsequently allowing the test solution to pass through a labeled antibody and consequently enabling observation of color development or light emission on a test line. The test solution and the labeled antibody may be supplied to the supporting body after they have been mixed in advance to form a specimen-labeled antibody complex. Also in the case of adopting the immunoassay method that employs the flow-through process, by causing the capturing antibody possessing a sensitizing action to be immobilized together with a capturing antibody or a capturing antigen on the test line, it is made possible to bring about color development of light emission intensely on the test line and realize the analysis with high sensitivity. Then, by adopting the flow-through process, it is made feasible to execute the analysis more rapidly as compared with the immunochromatography process.

While the foregoing explanation has cited the sandwich process as an example, this invention also allows adoption of the immunoassay method that employs a competitive process.

The competitive process first prepares a test line by causing a specimen and a marker substance to be jointly immobilized in advance on a supporting body. The immobilization of the specimen on the supporting body is preferably executed by a procedure that comprises mixing the marker substance with the solution of a proteinaceous substance thereby inducing combination of the marker substance with the proteinaceous substance and subsequently supplying the supporting body with the resultant solution. In consequence of this procedure, the marker substance possessing a sensitizing action can be stably immobilized on the supporting body. As the proteinaceous substance to be combined with the marker substance, bovine serum albumin may be cited, for example.

Next, a test solution containing a specimen at an unknown concentration and a labeled antibody capable of being specifically combined with the specimen are fed to the supporting body. The test solution and the labeled antibody may be fed to the supporting body after they have been mixed with each other to form a composite between the specimen and the labeled antibody. Otherwise, the test solution and the solution containing the labeled antibody may be separately fed sequentially in the order mentioned to the supporting body. When the specimen in the test solution has a low concentration, the labeled antibody that has not formed the composite with the specimen is accumulated in a large amount. On the other hand, when the specimen in the test solution has a high concentration, the labeled antibody is not accumulated on the test line but is migrated to the downstream side. As a result, the amount of the labeled antibody accumulated on the test line is increased and the intensity of the color development or light emission on the test line is exalted in accordance as the concentration of the specimen is decreased. By uniformizing such conditions as the concentration of the specimen to be immobilized and the concentration of the labeled antibody to be mixed with the test solution, therefore, it is made feasible to execute the quantitative analysis based on the intensity of color development or the intensity of light emission on the test line as an index.

In the immunoassay method employing the competitive process as described above, since the marker substance possessing a sensitizing action is immobilized together with the specimen in advance on the test line of the supporting body, the intensity of color development or the intensity of light emission caused by the labeled antibody (marker substance) on the test line is increased and the amount of the labeled antibody (marker substance) required for making the color development or light emission detectable is decreased. Further, owing to the presence of the immobilized marker substance, the intervals separating the marker substance grow in compactness and the state of having the labeled antibody accumulated in a high concentration is realized in a falsifiable manner. For this reason, the intensity of color development or the intensity of light emission is obtained emphatically on the test line even when the labeled antibody is accumulated in a small amount on the test line. As a result, the immunoassay method employing the competitive process allows the range of the determination on the high concentration side to be widened and the enlargement of the dynamic range to be anticipated.

EXAMPLES

Now, working examples of this invention will be explained in detail below.

(Experiment 1: Detection of hCG (human chorionic gonadotropin)) First, the detection of hCG that is the marker for a pregnancy test was studied as a model with a view to exalting the sensitivity of the immunochromatography method.

(Study of amount of colloidal gold particles to be applied to test line) First, the amount of a marker substance to be immobilized on the test line was studied. As the marker substance, colloidal gold particles of varying particle diameters (10 nm, 15 nm, 40 nm, 60 nm, 80 nm, and 150 nm) (made by BBI Corp.) were prepared. Then, as the capturing antibody, an anti-hαS antibody that is a monoclonal antibody capable of recognizing the α-subunit of hCG was prepared. A gold colloid-conjugated anti-hαS antibody was manufactured by modifying the colloidal gold particles with the anti-hαS antibody. Solutions containing gold colloid-conjugated anti-hαS antibodies in such amounts as to set the O.D. value (520 nm) at 6 were prepared and the solutions of colloidal gold particles of varying particle diameters were made to assume the same density of red color.

Next, mixed solutions were obtained by mixing the solutions containing the gold colloid-conjugated anti-hαS antibodies with the solutions containing non-labeled anti-hαS antibodies not modified with colloidal gold particles. Test lines were obtained by applying the mixed solutions each to a membrane by means of a spotter (made by Musashi Engineering K.K. and sold under the trademark designation of "Shot Master 3000"). In the adjustment of the mixed solutions mentioned above, the non-labeled anti-hαS antibody solutions were mixed with gold colloid-conjugated anti-hαS antibody solutions containing colloidal gold particles at varying concentrations of 1%, 3%, 5%, 10%, 20%, 50%, and 80%. The amount of such mixed solution applied to the membrane was set at 0.2 μl per spot. In this case, the concentrations of colloidal gold particles on the relevant test lines were estimated, on the assumption that the application was made at a yield of 100%, to be approximately 8 ng/mm$^2$, 24 ng/mm$^2$, 40 ng/mm$^2$, 80 ng/mm$^2$, 160 ng/mm$^2$, 400 ng/mm$^2$, and 6400 ng/mm$^2$ respectively. Incidentally, the statement "the non-labeled anti-hαS antibody solution is mixed with 5% of the gold colloid-conjugated anti-hαS antibody solution" means that 100 ml of the non-labeled anti-hαS antibody solution is mixed with 5 ml of the gold colloid-conjugated anti-hαS antibody solution.

Figure 4:
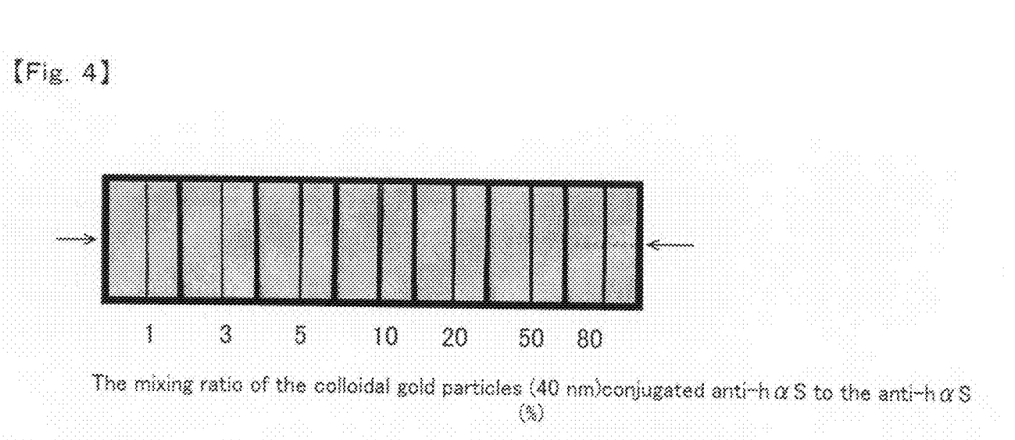
FIG. 4 This is a photograph showing the result of a study of the amount of colloidal gold particles (40 nm) applied to a membrane.

Subsequently, the test lines on the membranes were visually observed. FIG. 4 shows a photograph of a membrane using colloidal gold particles 40 nm in particle diameter as a marker substance. From FIG. 4, it is confirmed that when the amount of the gold colloid-conjugated anti-hαS antibody fell short of 5%, the color development of the colloidal gold particles could not be recognized by visual observation even if colloidal gold was applied in advance to the membrane. In the case of the other particle diameters similarly to the case of 40 mm, it is confirmed that the color development could not be recognized by visual observation when the amount of the gold colloid-conjugated anti-hαS antibody fell short of 5%, namely when the concentration of colloidal gold particles fell short of 40 ng/mm$^2$. It has been consequently ascertained that the amount of colloidal gold particles immobilized on the test line that falls short of 5%, namely 40 ng/mm$^2$, is the amount that inhibits the recognition by visual observation. The detection of hCG by the method to be described below resulted in confirming the fact that the assumption of a color induced by the non-specific adsorption between antibodies could be infallibly repressed by causing the amount of the gold colloid-conjugated anti-hαS antibody to fall short of 3%, namely 24 ng/mm$^2$.

(Preparation of hCG detection immunochromato strip) Next, an immunochromatography strip for use in the detection of hCG was prepared. A gold colloid-conjugated anti-hαS antibody was prepared by modifying an anti-hαS antibody with colloidal gold particles 60 nm in particle diameter. The solution containing the gold colloid-conjugated anti-hαS antibody was adjusted so that the O.D.$_{520}$ would be set at 6 and this solution was mixed with a solution containing a non-labeled anti-hαS antibody to obtain a mixed solution. The mixing ratio of the gold colloid-conjugated anti-hαS antibody solution to the non-labeled anti-hαS antibody solution was set at 3%.

The mixed solution mentioned above was applied to the position of the membrane fated to form a test line by the use of the product of BioDot Corp. sold under the trademark designation of "BioJet Quanti 300." The amount of this mixed solution to be applied was set at 0.7 μl per cm. The mixed solution was applied, dried, and subsequently subjected to blocking and washing. The resultant membrane was applied to a backing sheet and, after having an absorption pad attached to the terminal part thereof, was sliced into strips 4 mm in width to obtain hCG detection immunochromato test strips.

(Determination of hCG) A recombinant hCG (made by Rhoto K.K.) was diluted with a phosphate buffer at ratios calculated to give concentrations of 0.1 ng/ml, 0.05 ng/ml, 0.025 ng/ml, 0.0125 ng/ml, 0.00625 ng/ml, and 0.00315 ng/ml. The diluted hCG solutions consequently obtained were used as test solutions in the experiment.

As the labeled antibody aimed at detecting the hCG, the gold colloid-conjugated anti-hαS antibody was used. The anti-hCG antibody was a monoclonal antibody capable of recognizing the β-subunit of hCG. The solution containing the gold colloid-conjugated anti-hαS antibody was adjusted so that the O.D.$_{520}$ would be set at 6.

Figure 5:
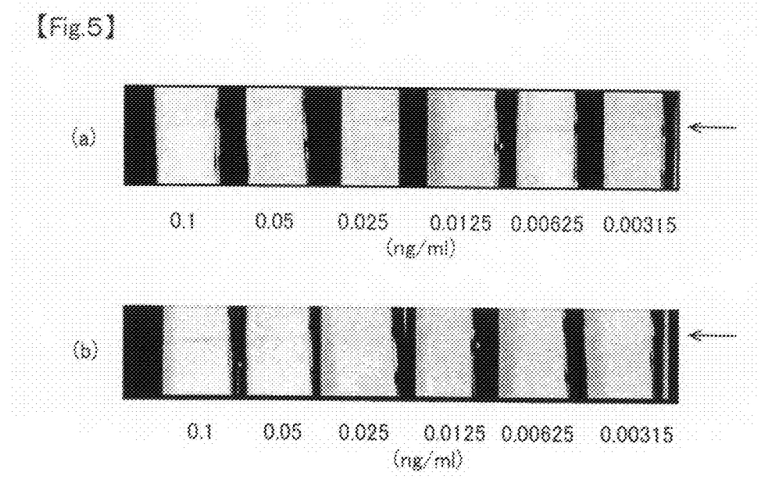
FIG. 5 (*a*) This is a photograph showing the result of detection of human chorionic gonadotropin (hCG) by the use of an immunochromato test strip (working example) of this invention and (b) this is a photograph showing the result of detection of hCG by the use of a conventional immunochromato test strip (comparative example). The numerals given therein indicate hCG concentrations in a test solution and the arrow marks indicate test lines.

To 40 μl of the relevant hCG diluted solution (test solution), 4 μl of the aforementioned solution containing the gold colloid-conjugated anti-hαS antibody (labeled antibody) was added. These two solutions were mixed and the resultant mixed solution was absorbed by the hCG detection immunochromato strip mentioned above at one terminal thereof to execute detection of hCG. The results are shown in FIG. 5 (a).

For the sake of comparison, an immunochromato test strip was prepared by the ordinary method. To be specific, the test line was not coated with colloidal gold particles as a marker substance but was coated solely with an anti-hαS antibody serving as a capturing antibody, which was immobilized on the test line. This immunochromato test strip was used similarly to the procedure explained above to implement the detection of hCG. The results are shown in FIG. 5 (b).

With the conventional immunochromato test strip, the color development on the test line became difficult of recognition at the stage of 0.025 ng/ml and it could not be recognized by visual observation at a concentration falling short of this stage. In contrast, in the case of using the immunochromato test strip of this invention, the color development on the test line could be clearly recognized by visual observation even at such a low concentration of 0.00315 ng/ml.

(Study of particle diameter of immobilized colloidal gold particles) A study was made in search of the optimum particle diameter of colloidal gold particles to be immobilized on the membrane. First, colloidal gold particles having particle diameters of 5 nm, 15 nm, 40 nm, 60 nm, and 80 nm were prepared and anti-hαS antibodies were modified with the colloidal gold particles of these varying particle diameters to obtain gold colloid-conjugated anti-hαS antibodies. The solutions containing these gold colloid-conjugated anti-hαS antibodies were adjusted so that the O.C.$_{520}$ would be set at 6. They were mixed with solutions containing non-labeled anti-hαS antibodies to obtain mixed solutions. The mixing ratio of the gold colloid-conjugated anti-hαS antibody solutions to the non-labeled anti-hαS antibody solutions was set at 3%, ie the level at which the color development on the control line could not be recognized by visual observation. Then, in conformity with the procedure for the manufacture of hCG detection immunochromato strips explained above, hCG detection immunochromato strips were manufactured by using the mixed solutions obtained above.

Figure 6:
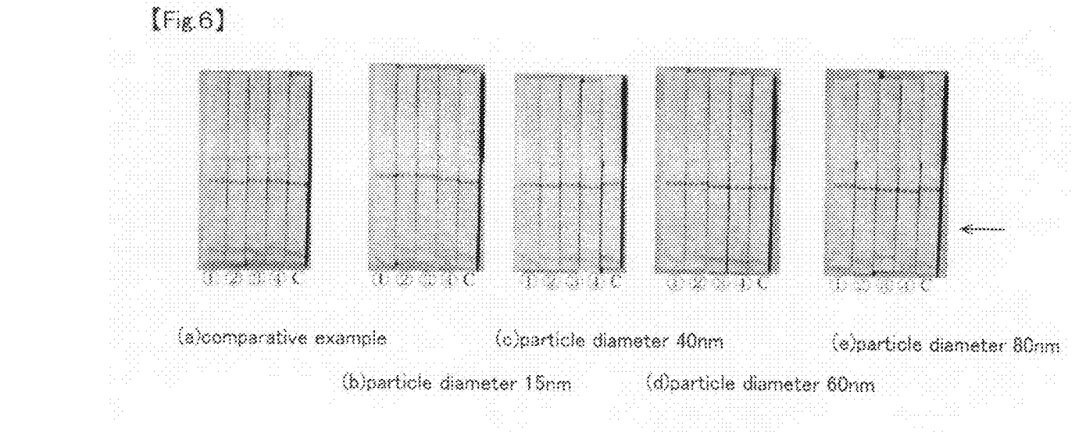
FIG. 6 This is a photograph showing the result of detection of hCG in a phosphate buffer having varied the particle diameter of colloidal gold particles immobilized on an immunochromato test strip; (a) representing the result of using the conventional immunochromato test strip (comparative example), (b) the result of immobilizing colloidal gold particles having a particle diameter of 15 nm, (c) the result of immobilizing colloidal gold particles having a particle diameter of 40 nm, (d) the result of immobilizing colloidal gold particles having a particle diameter of 60 nm, and (e) the result of immobilizing colloidal gold particles having a particle diameter of 80 nm. The arrow mark shown therein indicates the test line.

Next, dilute hCG antigen solutions were manufactured by using a phosphate buffer and these dilute solutions were used as test solutions to execute detection of hCG. The results are shown in FIG. 6. In the drawing, 1, 2, 3, 4, and C are signs for denoting the hCG concentrations, respectively 1 ng/ml, 0.1 ng/ml, 0.01 ng/ml, 0.001 ng/ml, and 0 (containing no hCG), in the test solutions spread on the relevant strips.

It is clear from FIG. 6 that in all the particle diameters invariably, the sensitivity of detection was exalted by having the colloidal gold particles immobilized in advance on the relevant test lines. Particularly when the colloidal gold particles having particle diameters of 14 nm ~40 nm among other particles diameters involved herein were immobilized, the coloration on the test lines was observed far more clearly and the detection with much higher sensitivity was realized even in case where the concentrations of hCG were extremely low. The highest sensitivity was obtained particularly when the colloidal gold particles having a particle diameter of 15 nm were immobilized. Incidentally, the effect of exalting the sensitivity of detection was insufficient when the colloidal gold particles having a particle diameter of 5 nm were immobilized.

(Study of Particle Diameter of Immobilized Colloidal Gold Particles Using Serum) First, hCG detection immunochromato strips were manufactured similarly to the case of preparing test solutions by the use of a phosphate buffer. The colloidal gold particles having particle diameters of 15 nm, 40 nm, and 60 nm were immobilized on the relevant test lines.

Figure 7:
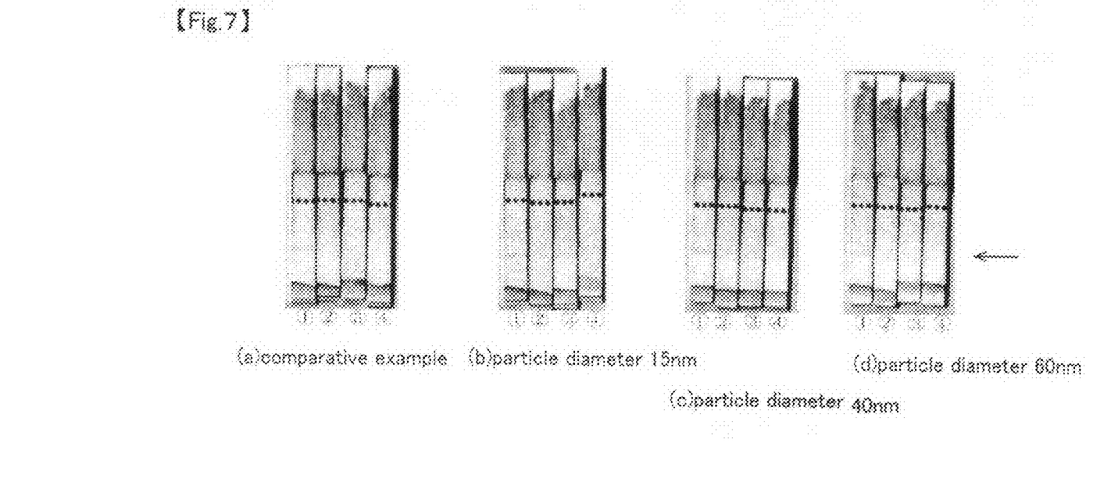
FIG. 7 This is a photograph showing the result of detection of hCG in a male blood serum having varied the particle diameter of colloidal gold particles immobilized on an immunochromato test strip; (a) representing the result of using the conventional immunochromato test strip (comparative example), (b) the result of immobilizing colloidal gold particles having a particle diameter of 15 nm, (c) the result of immobilizing colloidal gold particles having a particle diameter of 40 nm, and (d) the result of immobilizing colloidal gold particles having a particle diameter of 60 nm. The arrow mark shown therein indicates the test line.

Next, dilute hCG antigen solutions were prepared by using male serum and these dilute solutions were used as test solutions to execute detection of hCG. The results are shown in FIG. 7. In the drawing, 1, 2, 3, and 4 are signs for denoting the hCG concentrations, respectively 1 ng/ml, 0.1 ng/ml, 0.01 ng/ml, and 0.001 ng/ml, in the test solutions spread on the relevant strips.

It is clear from the results given in FIG. 7 that when serum was used as a test solution, the detection with high sensitivity was realized similarly to the case of using a phosphate buffer and particularly when colloidal gold particles having particle diameters of 15 nm~40 nm were immobilized, the detection with still higher sensitivity was realized. The best results were obtained when colloidal gold particles having a particle diameter of 15 nm were immobilized.

(Experiment 2: Detection of PSA (prostate specific antigen)) The PSA that is the index of the cancer of the prostate cancer exists, though slightly, even in a healthy male and grows in extent with age. When the value of this PSA is 4 ng/ml or more, it justifies a doubt regarding the cancer of the prostate gland in the initial phase and urges the health examination to conduct a secondary test. Thus, the immunochromatography strips are preferred to be capable of allowing accurate detection of the PSA falling short of 4 ng/ml in the serum test. The following experiment, therefore, was aimed at detecting the PSA with high sensitivity.

(Preparation of PSA detection immunochromato test strips) First, an immunochromatography strip intended for the detection of PSA was prepared by using colloidal gold particles (40 nm) as a marker substance and as well using an anti-PSA antibody as a capturing antibody.

For the purpose of immobilizing the marker substance on a membrane, a gold colloid (15 nm)-conjugated anti-PSA antibody (capturing antibody) was prepared by modifying an anti-PSA antibody (capturing antibody) with colloidal gold particles (15 nm). The solution containing the prepared gold colloid (15 nm)-conjugated anti-PSA antibody was adjusted so that the $O.D._{520}$ would be set at 6. Next, the solution containing the gold colloid (15 nm)-conjugated anti-PSA antibody mentioned above was mixed at a ratio of 3% to a solution containing a non-labeled ant-PSA antibody to obtain a mixed solution. A PSA detection grade immunochromato test strip was obtained by applying the mixed solution to a membrane similarly to Experiment 1.

(Detection of PSA) Then, detection of PSA in blood was tried. Since the prostate cancer is a disease peculiar to a male individual, the PSA is not detected normally in the blood of a female individual. So, the PSA was added to the blood of a female individual in amounts so calculated as to equal concentrations of 1 ng/ml and 0.1 ng/ml. The products of this addition were used as test solutions.

As the labeled antibody for the detection of PSA, a gold colloid (40 nm)-conjugated anti-PSA antibody was obtained by modifying the anti-PSA antibody with colloidal gold particles (40 nm). The anti-PSA antibody used herein was such that it would be combined with the PSA at a different site from the anti-PSA antibody (15 nm) serving as the capturing antibody mentioned above. The solution containing the gold colloid (40 nm)-conjugated anti-PSA antibody was so adjusted that the $O.D._{520}$ would be set at 6.

Thereafter, 4 µl of the solution containing gold colloid (40 nm)-conjugated anti-PSA antibody was added to 40 µl of the blood of a female individual mixed with PSA and these solutions were mixed. Then, the PSA detection immunochromato test strip was caused to absorb the resultant mixed solution to execute detection of PSA.

Figure 8:
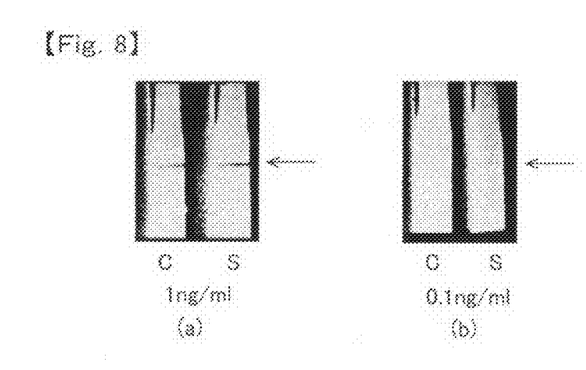
FIG. 8 This is a photograph showing the result of detection of prostate specific antigen (PSA) by the use of a PSA detection immunochromato test strip; (a) representing the result of detection of PSA of a concentration of 1 ng/ml and (b) the result of detection of PSA of a concentration of 0.1 ng/ml. The letter S shown therein denotes an immunochromato test strip and the letter C the conventional immunochromato test strip. The arrow marks shown therein indicate a test line each.

For the purpose of comparison, an immunochromato test strip was prepared by the conventional method. Specifically, the test line was not coated with colloidal gold particles but was coated solely with an anti-PSA antibody serving as a capturing antibody, which was immobilized thereon. The immunochromato test strip thus completed was subjected to detection of PSA similarly to the procedure explained above. The results are shown in FIG. 8. In FIG. 8, S denotes the immonochromato test strip of this invention and C the conventional immunochromato test strip.

It is clear from FIG. 8 that in the immunochromato test strip prepared by the conventional method, the coloration of the test line was recognized by visual observation when the PSA concentration was 1 ng/ml, whereas the coloration of the test line could not be recognized when the concentration of PSA was 0.1 ng/ml. On the other hand, when the immunochromato test strip of this invention was used, the test line could be recognized even when the concentration of PSA was 0.1 ng/ml. By the results of Experiment 2, therefore, it is ascertained that the immunochromato test strip of this invention was capable of detecting PSA with high sensitivity and was useful for convenient and accurate diagnosis of the prostate cancer in the initial phase.

From the results of Experiment 1 and Experiment 2 described above, it is ascertained that the exaltation of sensitivity of the immunochromatography strip was realized by having a marker substance immobilized in advance together with a capturing antibody.

(Experiment 3: Study of amount of capturing antibody to be immobilized) In the following experiment, a study was performed to determine whether or not the immunochromato test strip conforming to this invention allowed a decrease in the amount of a capturing antibody to be immobilized on the test line.

(Preparation of PSA detection immunochromato test strip) An immunochromatography strip aimed at detecting PSA was prepared by using colloidal gold particles (15 nm) as a marker substance and as well using an anti-PSA antibody as a capturing antibody.

A conventional immunochromatography strip was completed by preparing an anti-PSA antibody solution having a concentration of 650 ng/ml and applying this solution to a test line. Then, anti-PSA antibody solutions containing an anti-PSA antibody in concentrations of 430 ng/ml (66% based on an anti-PSA antibody solution having a concentration of 650 ng/ml taken as 100%), 325 ng/ml (50%), and 215 ng/ml (33%) were prepared. Mixed solutions were obtained by adding 3% of a solution (O.D.$_{520}$) containing gold colloid-conjugated anti-hαS antibody to the solutions. These mixed solutions were applied severally to a membrane similarly to Example 2 described above to obtain PSA detection immunochromato test strips.

Figure 9:
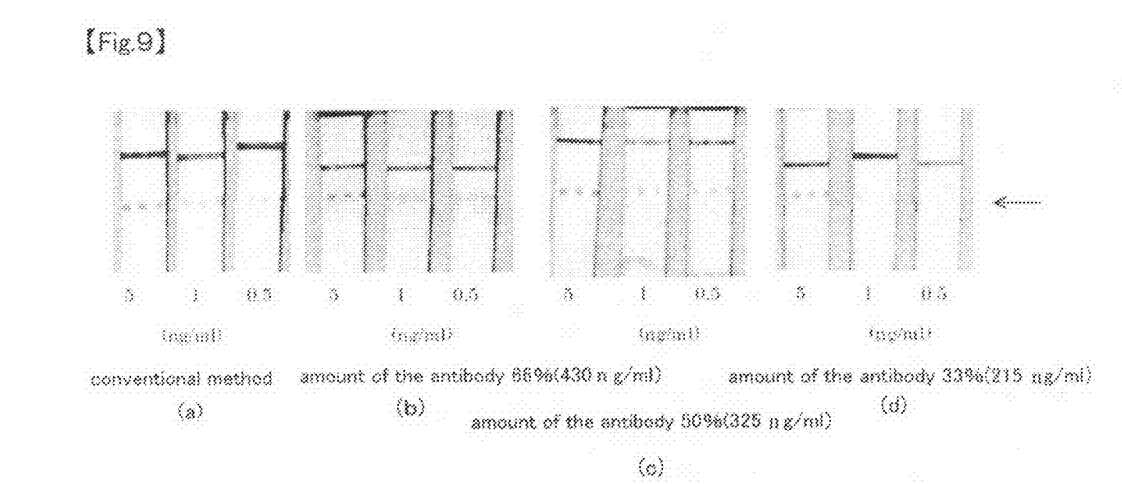
FIG. 9 This is a photograph showing the result of a test of Example 3; (a) representing the result of using a conventional immunochromato test strip (comparative example), (b) the result of setting the amount of a capturing antibody at 66% of that of (a), (c) the result of setting the amount of the capturing antibody at 50% of that of (a), and (d) the result of setting the amount of the capturing antibody at 33% of that of (a). The arrow mark shown therein indicates a test line.
Figure 10:
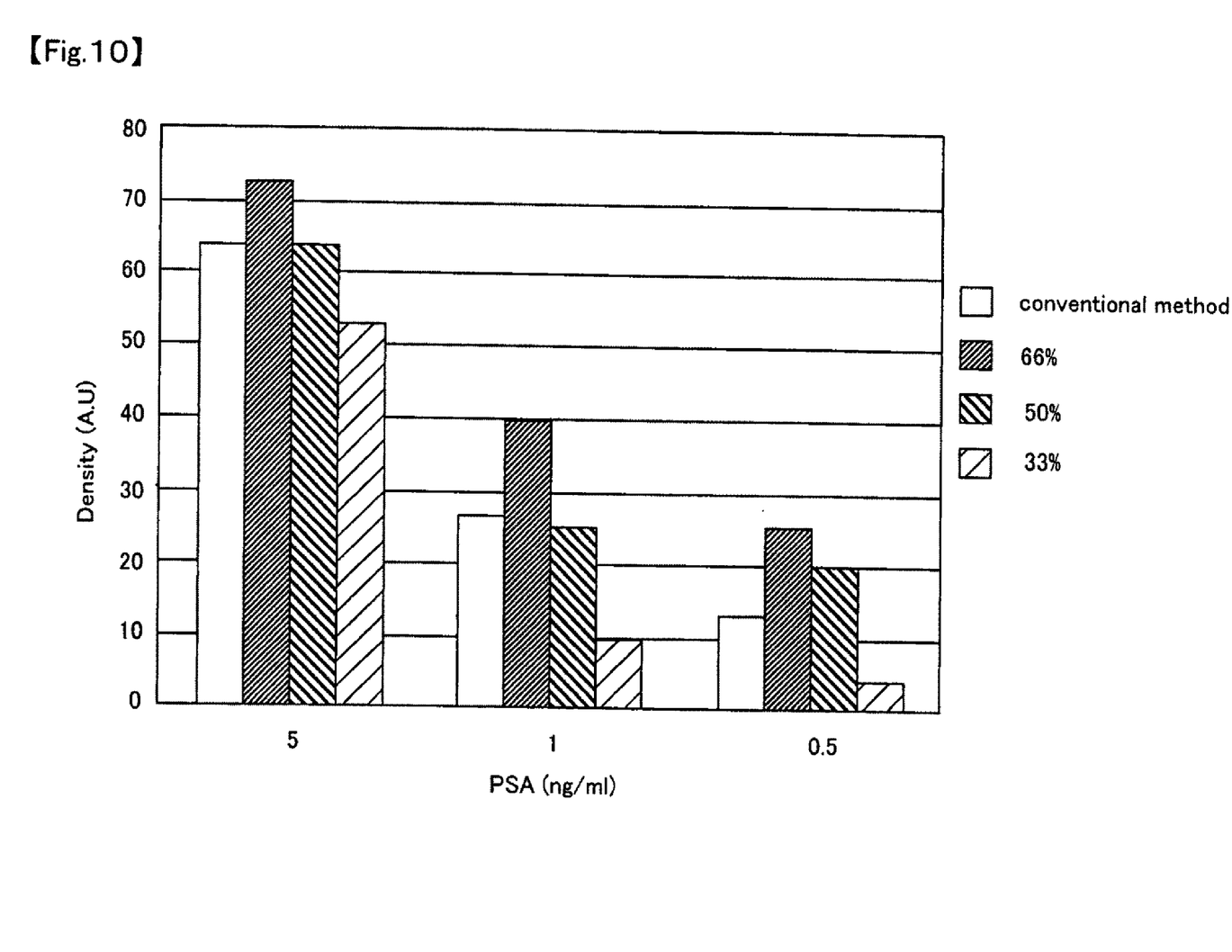
FIG. 10 This is a diagram showing the relation between the concentration of PSA and the intensity of color development of an immunochromato test strip on the test line, ie the result of comparing the conventional method and the method embodying this invention.

Thereafter, detection of PSA was performed similarly to Example 2. PSA solutions having concentrations of 5 ng/ml, 2 ng/ml, and 0.5 ng/ml were severally studied. The photographs of the strips subsequent to the analysis are shown in FIG. 9. Then, the colors of the relevant test lines were tested for density with a densitometer, subjected to image analysis, and compared. The results are shown in FIG. 10.

Even when the amount of the capturing antibody to be immobilized on the test line of the membrane was decreased to 66% of the conventional level, the sample of this decreased capturing antibody was enabled by having colloidal gold particles immobilized in advance on the test line to yield the coloration of higher intensity than the conventional sample having no colloidal gold particles immobilized on the test line. Also when the amount of the capturing antibody to be immobilized on the test line was decreased to 50% of the conventional level, the sample of this decreased capturing antibody was enabled by having colloidal gold particles immobilized in advance on the test line to yield the coloration of equal intensity to the sample having the amount of capturing antibody set at 100%. In the immunochromato test strip, the antibody is one of the most expensive materials. This invention, therefore, is expected to allow a copious reduction of the cost of the immunochromato test strip because it is capable of realizing the same sensitivity as has been attained before even when the amount of a capturing antibody to be required is decreased to nearly half of the conventional level.

The invention claimed is:

1. A method for analyzing a specimen by an immunoassay process, comprising:
   obtaining a supporting body comprising a test line having a capturing antibody or capturing antigen adapted to be specifically combined with the specimen, and a marker substance possessing a sensitizing action and coexisting with the capturing antibody in case of using the capturing antibody or with the capturing antigen in case of using the capturing antigen,
   providing a complex material including the specimen and a labeled antibody specifically combining with the specimen and forming another marker substance, to the test line of the supporting body,
   capturing the specimen of the complex material by the test line to thereby accumulate the labeled antibody on the test line so that a color development or light emission obtained by the marker substance on the test line is added with a color development or light emission originating from the another marker substance forming the labeled antibody to thereby increase the color development or light emission originating from the labeled antibody accumulated on the test line, and
   detecting the increased color development or light emission obtained by the test line to analyze the specimen.

2. The method for analyzing a specimen according to claim 1, wherein said immunoassay process is performed as a part of a sandwich process.

3. The method for analyzing a specimen according to claim 1, wherein said immunoassay process is performed as a part of a competitive process.

4. The method for analyzing a specimen according to claim 1, wherein in obtaining the supporting body, a solution containing said capturing antibody or said capturing antigen and said marker substance is applied to said supporting body.

5. The method for analyzing a specimen according to claim 1, wherein a color-developing substance or light-emitting substance is used as the another marker substance forming the labeled antibody and the marker substance.

6. The method for analyzing a specimen according to claim 1, wherein noble metal colloidal particles are used as the marker substance, and latex particles are used as the another marker substance forming the labeled antibody or antigen.

7. The method for analyzing a specimen according to claim 1, wherein the test line includes the marker substance thereon in an amount such that the color development or light emission is incapable of being recognized by visual observation.

8. The method for analyzing a specimen according to claim 7, wherein colloidal gold particles are used as the marker substance.

9. The method for analyzing a specimen according to claim 1, wherein the color development or light emission on said test line is analyzed with an instrument, and an amount of said marker substance deposited on said test line when the supporting body is obtained is not more than a detection limit of the color development or light emission of said instrument.

10. The method for analyzing a specimen according to claim 5, wherein a combination of the marker substance and the another marker substance forming the labeled antibody is selected from the group consisting of a combination of finely divided silver particles and finely divided gold particles, a combination of finely divided gold particles and finely divided latex particles, a combination of finely divided gold particles and finely divided fluorescent particles, and a combination of finely divided gold particles and finely divided liposome including silver particles.

* * * * *